United States Patent [19]

Silver

[11] Patent Number: 4,811,739

[45] Date of Patent: Mar. 14, 1989

[54] METHOD AND APPARATUS FOR THE DETERMINATION OF SUBSTANCES IN HUMAN FLUIDS

[76] Inventor: Robert H. Silver, 5913 Hillview Park, Van Nuys, Calif. 91401

[21] Appl. No.: 158,024

[22] Filed: Feb. 12, 1988

Related U.S. Application Data

[63] Continuation of Ser. No. 414,928, Sep. 3, 1982, abandoned, Continuation of Ser. No. 866,502, Jan. 3, 1975, abandoned.

[51] Int. Cl.⁴ ............................................. A61B 3/14
[52] U.S. Cl. ..................................... 128/664; 351/221
[58] Field of Search ..................... 128/664, 665, 745; 351/221

[56] References Cited

U.S. PATENT DOCUMENTS

| | | | |
|---|---|---|---|
| 2,536,305 | 1/1951 | Morton | 351/221 X |
| 3,036,568 | 5/1962 | Stark | 128/664 |
| 3,462,604 | 8/1969 | Mason | 250/206 |
| 3,572,910 | 3/1971 | Charles | 351/221 X |
| 3,879,113 | 4/1975 | Howland et al. | 351/221 X |
| 3,925,793 | 12/1975 | Matsumura et al. | 351/206 X |

FOREIGN PATENT DOCUMENTS 116633 12/1957 U.S.S.R. ........................... 128/2 T

Primary Examiner—Edward M. Coven
Attorney, Agent, or Firm—Freilich, Hornbaker, Rosen & Fernandez

[57] ABSTRACT

A method and apparatus for determining the presence of substances in human fluids, utilizing variable wavelength beam of light, which is analyzed by spectrographic methods after passage through the vitreous humor of the eye.

16 Claims, 1 Drawing Sheet

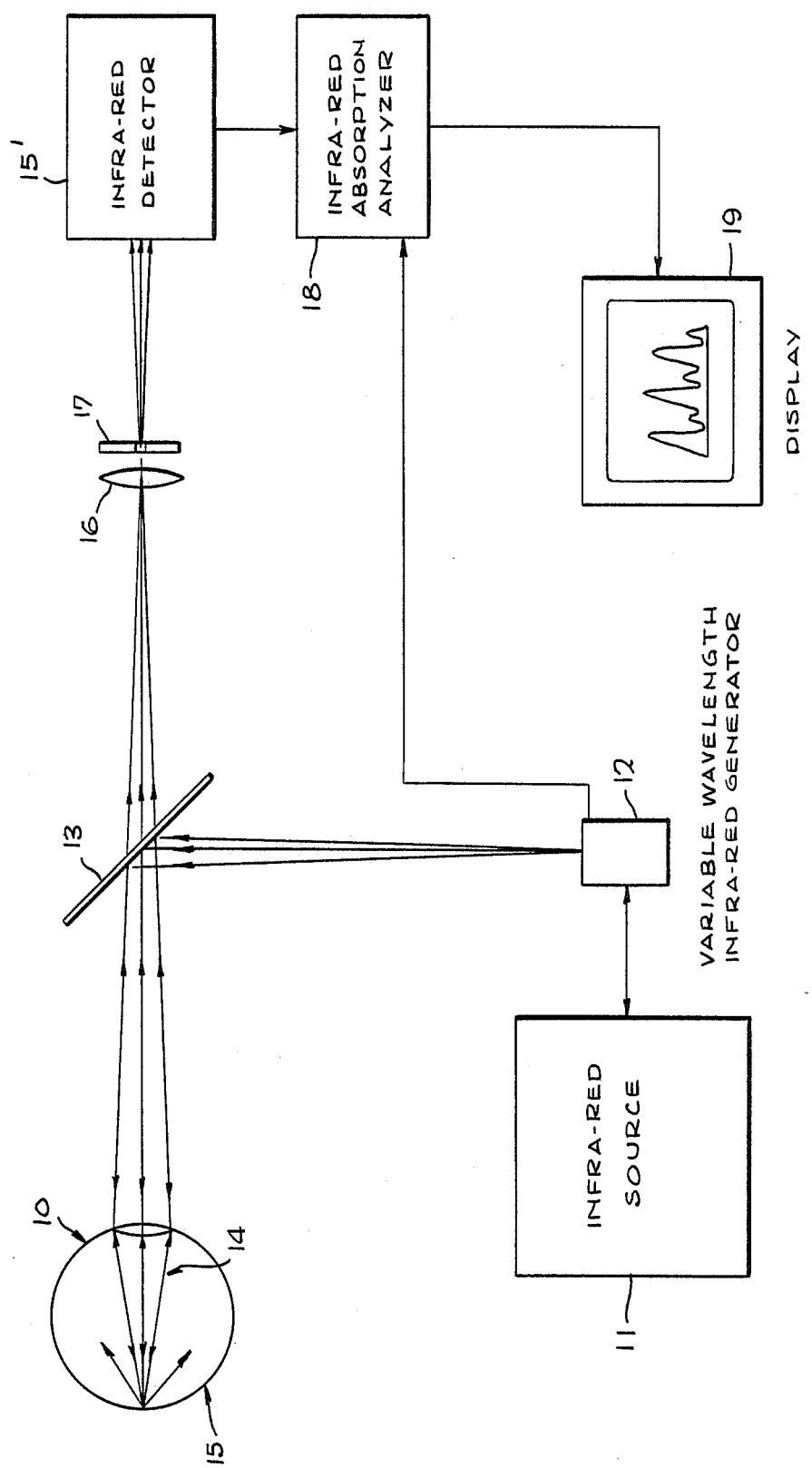

METHOD AND APPARATUS FOR THE DETERMINATION OF SUBSTANCES IN HUMAN FLUIDS

This is a continuation of Ser. No. 414928, filed Sept. 3, 1982 abandoned, which is a continuation of application Ser. No. 866,502 filed Jan. 3, 1978, abandoned.

BACKGROUND OF THE INVENTION

To determine the presence of minute quantities of substances, such as alcohol, narcotics, drugs, or toxins in human body fluids, such as blood, several state-of-the-art methods have been utilized. Each of these methods have various disadvantages. Some methods involve obtaining a sample of body fluid, such as blood, which requires an invasive technique. There are public policy and legal problems associated with invasive techniques. When methods employing non-invasive techniques are used there are problems of inconvenience and/or inaccuracy. This is especially true in the determination of blood alcohol of persons suspected of being under the influence of intoxicating beverages. Some characteristic problems include contamination of the sample taken by substances not found in the body fluids, inaccuracy of the measurements, and subject resistance or non-cooperation. The present invention will eliminate many, if not all of the present problems encountered by forensic toxicologists and law enforcement officials associated with the in-field toxicity determinations especially as applied to so-called drunk driving or driving under the influence cases.

While law enforcement has in the past been primarily concerned with determining the presence and concentration of alcohol in the blood, the use by the public of other substances has led to the need to detect their presence. These substances include numerous narcotics, drugs, or their immediate precursors, all of which are referred to as "controlled substances." Such controlled substances or their products of decomposition include methadone, morphine, codeine, marijuana, amphetamines, barbiturates, and hallucinogenic substances. A complete schedule of such substances is specified in Sections 11034 through 11038 of the California Health and Safety Code.

Not only has there been an increase in the substances used but the wide variation in types of substances has made detection difficult. For example, non-invasive breath analysis is totally ineffective in detecting the presence of a large number of the diversified substances currently being used. Urine analysis, while capable of detecting the presence of more substances, has problems of practicality, accuracy, and speed. A urine analysis, as with other current techniques, also presents the problems of subjects objecting to providing samples.

Another problem with non-invasive breath analysis concerns accuracy. This method is considered inaccurate unless a number of tests are conducted over a period of time. The reason for this is that the recent consumption of alcohol, the occurance of gastric disturbances such as belching, or the use of alcohol containing mouth wash render the results inaccurate.

A still further disadvantage of current detection systems involves portability. Law enforcement officials generally need to determine the presence of substances in the fluids at the time of an offense. For example, in those of an operator of a motor vehicle. In order to obtain an accurate determination of the presence of various substances, the current practice is to transport the operator to a station house remote from the roadway where the operator was apprehended. The loss of time and inefficiency of such a procedure is readily apparent.

When alcohol or controlled substances are introduced into the human body and into the body's fluidic systems, they are also introduced into the vitreous humor of the eyeballs. Furthermore, the concentration of the substance in the vitreous humor is related to the concentration in the body itself. Thus, an examination of the vitreous humor can provide information on the presence and concentration of alcohol or controlled substances in the body.

SUMMARY OF THE INVENTION

Briefly, the present invention comprises a method and optical system in which a variable wavelength light beam is directed at the vitreous humor of the subject's eyeball. While the invention encompasses light of any wavelength, existing technology lends itself to practicing the invention using light of the infrared spectrum. Therefore, while not limited to infrared light, the invention is described using infrared light. The infrared light, after passing through the vitreous humor portion of the eye, is reflected by the retina at the back of the eye. The reflected beam of infrared light is directed to an infrared detector or sensor. At the detector, the absorption of various wavelengths by the presence of minute amounts of various substances in the vitreous humor, is sensed and measured and the results are displayed by means of a recorder, digital display, or other display instrument.

One object of the invention is to provide an accurate, non-invasive means for determining the presence and concentration of substances in body fluids.

Another object of the invention is to provide a portable and versatile means for determining the presence and concentration of diverse substances in body fluids.

A still further object of the invention is to provide a non-objectionable means for determining the presence and concentration of substances in body fluids.

Other objects and advantages will become apparent to those skilled in the art upon consideration of the following description and drawing.

BRIEF DESCRIPTION OF THE DRAWING

The drawing is a schematic drawing showing the major optical components of my invention.

DESCRIPTION OF THE PREFERRED EMBODIMENT

In the drawing an eyeball 10 is schematically shown. Infrared (IR) light (radiation) from an infrared source 11 is directed to a variable wavelength IR generator 12. Variable IR generator 12 may comprise a rotating refraction grating the output of which is a variable wavelength infrared beam which is scanned through a suitable wavelength band. The variable wavelength infrared light beam is directed to beam splitter 13 where it illuminates the eyeball 10. The infrared beam of light passes through the vitreous humor portion of the eye 14 and is reflected from the retina 15 at the back of the eye causing it to again pass through the vitreous humor 14. The beam of light emerging from the eyeball 10 passes through beam splitter 13 and is directed to infrared detector 15'. A lens 16 and aperture 17 may be employed to focus the beam and cutout extraneous light. The output of infrared detector 15' is directed to absorption analyzer 18 which measures a physical property, the absorption of infrared energy following the well known Beer-Lambert law of absorption. The relative absorption of various infrared wavelengths, caused by the minute amounts of substances contained in the vitreous humor, which indicates the presence and concentration of the substances in the various body fluids, is displayed on a recorder or other conventional display 19. A portion of the variable wavelength infrared beam from variable IR generator 12 is also directed to absorption analyzer 18 to provide an unabsorbed signal for comparison. Instead of feeding a portion of the beam to absorption analyzer 18, an indication of the wavelength and amplitude of the infrared beam could be provided to analyzer 18. In fact, the invention can be practiced by analyzing the reflected beam without any additional indication from the variable infrared generator 12. The presence and concentration of substances in the vitreous humor, and therefore in body fluids, are determined from an analysis of the absorption record chart or by other display techniques using well known infrared spectographic methods. While the invention is described using a variable wavelength beam, if detection of only the presence of a particular substance is desired, then a fixed wavelength beam may be employed. Furthermore, while the described embodiment of the invention has been discussed in the context of foreign substances introduced into the body fluids, my invention can also detect the presence and concentration of substances produced by the body as a result of such conditions as illness, disease, other abnormalities, or aging for diagnostic purposes. It is evident that various modifications may be made to the apparatus disclosed herein without departing from the spirit and scope of the invention. Consequently, I do not intend the present invention to be limited to the particular embodiment and apparatus shown in the drawing, but rather by the appended claims.

What is claimed is:

1. An apparatus for determining the presence of substances in the vitreous humor of the eye of a subject wherein the absorption of light passing through the vitreous humor of the eye is analyzed comprising in combination:
   (a) means for generating incident light;
   (b) optical means for focusing said incident light through the pupil and the vitreous humor of the eye of a subject and onto the retina of the eye; and
   (c) means for measuring the intensity of the incident light that is reflected from the retina back through the vitreous humor and pupil of the eye, and for comparing the intensity of the reflected light with the intensity of the incident light in order to determine the amount of absorption of the incident light passing through the vitreous humor of the eye.

2. The apparatus of claim 1 in which said optical means comprises means for focusing said incident light entirely through the pupil and vitreous humor of the eye of a subject and onto the retina of the eye.

3. The apparatus of claim 2 in which said incident light is infrared light.

4. The apparatus of claim 2 in which said means for generating incident light comprises a source of variable wavelength light.

5. The apparatus of claim 2 in which said means for generating incident light comprises a source of variable wavelength infrared light.

6. The apparatus of claim 5 in which an indication of the wavelength and amplitude of the incident infrared light is provided to said means for measuring the intensity of the incident light that is reflected from the retina back through the vitreous humor and pupil of the eye, and for comparing the intensity of the reflected light with the intensity of the incident light in order to determine the amount of absorption of the incident light passing through the vitreous humor of the eye.

7. The apparatus of claim 2 in which said means for measuring the intensity of the incident light that is reflected from the retina back through the vitreous humor and pupil of the eye, and for comparing the intensity of the reflected light with the intensity of the incident light in order to determine the amount of absorption of the incident light passing through the vitreous humor of the eye includes display means for displaying the amount of absorption of the incident light.

8. The apparatus of claim 1 in which said incident light is infrared light.

9. The apparatus of claim 1 in which said means for generating incident light comprises a source of infrared light and a beam splitter positioned to reflect light from said source into the eye and to permit the light reflected from the retina to impinge upon the detection means.

10. The apparatus of claim 1 in which said means for measuring the intensity of the incident light that is reflected from the retina back through the vitreous humor and pupil of the eye, and for comparing the intensity of the reflected light with the intensity of the incident light in order to determine the amount of absorption of the incident light passing through the vitreous humor of the eye includes display means for displaying the amount of absorption of the incident light.

11. A method for determining the presence of substances in the vitreous humor of the eye of a subject wherein the absorption of light passing through the vitreous humor of the eye is analyzed comprising steps of:
    (a) focusing light through the pupil and vitreous humor of the eye of a subject and onto the retina of the eye;
    (b) detecting and measuring the intensity of the light reflected from the retina back through the vitreous humor and pupil of the eye; and
    (c) comparing the intensity of the reflected light with the intensity of the incident light in order to determine the amount of absorption of the incident light passing through the vitreous humor of the eye.

12. The method of claim 11 which includes comparing the intensity of the light detected with the intensity of the light directed through the pupil in order to determine the amount of light absorbed by the vitreous humor to thereby determine the presence of substances in the vitreous humor of the eye.

13. The method of claim 12 in which the light is infrared light.

14. The method of claim 12 in which the light is variable wavelength infrared light.

15. The method of claim 11 in which the light is variable wavelength light.

16. The method of claim 11 wherein the light is focussed entirely through the pupil and vitreous humor of the eye of a subject and onto the retina of the eye.

* * * * *